US009254382B2

(12) United States Patent
Ahmad et al.

(10) Patent No.: US 9,254,382 B2
(45) Date of Patent: Feb. 9, 2016

(54) APPARATUS FOR TRANSCUTANEOUS ELECTRICAL STIMULATION OF THE TIBIAL NERVE

(71) Applicant: Neurowave Medical Technologies LLC, Chicago, IL (US)

(72) Inventors: Aftab Ahmad, Chicago, IL (US); Matthew J. Geary, Chicago, IL (US); Farhan Hussain, Chicago, IL (US)

(73) Assignee: ReliefBand Technologies LLC, Jenkintown, PA (US)

( * ) Notice: Subject to any disclaimer, the term of this patent is extended or adjusted under 35 U.S.C. 154(b) by 0 days.

(21) Appl. No.: 14/177,133

(22) Filed: Feb. 10, 2014

(65) Prior Publication Data

US 2014/0228927 A1   Aug. 14, 2014

Related U.S. Application Data

(60) Provisional application No. 61/762,825, filed on Feb. 8, 2013.

(51) Int. Cl.
*A61N 1/00*     (2006.01)
*A61N 1/36*     (2006.01)
*A61H 39/00*    (2006.01)
*A61N 1/04*     (2006.01)

(52) U.S. Cl.
CPC .......... *A61N 1/36014* (2013.01); *A61H 39/002* (2013.01); *A61N 1/0456* (2013.01); *A61H 2201/164* (2013.01); *A61H 2201/165* (2013.01); *A61H 2205/125* (2013.01)

(58) Field of Classification Search
CPC .................................................... A61N 1/0476
USPC ............................................... 607/2, 72, 148
See application file for complete search history.

(56) References Cited

U.S. PATENT DOCUMENTS

| 4,981,146 A | 1/1991 | Bertolucci |
| 6,076,018 A | 6/2000 | Sturman et al. |
| 6,735,480 B2 | 5/2004 | Giuntoli et al. |
| 7,127,288 B2 | 10/2006 | Sturman et al. |
| 2003/0004555 A1* | 1/2003 | Giuntoli et al. ................. 607/72 |

OTHER PUBLICATIONS

A.E. Ridout et al., "Tibial nerve stimulation for overactive bladder syndrome unresponsive to medical therapy", Journal of Obstetrics & Gynaecology, Feb. 2010, vol. 30, No. 2 : p. 111-114.
Peters et. al., "Randomized Trial of Percutaneous Tibial Nerve Stimulation Versus Sham Efficacy in the Treatment of Over Active Bladder Syndrome: Results from SUmit Trial", Journal of Urology, vol. 183, Apr. 2010, p. 1438-1444.
MacDiarmid, S.A. et al. "Long-Term Durability of Percutaneous Tibial Nerve Stimulation for the Treatment of Overactive Bladder" (2010). J Urol, 183, p. 234-240.
Andreas Kuhn, "Modeling Transcutaneous Electrical Stimulation", ETH Zurich PhD Dissertation 2008.

* cited by examiner

*Primary Examiner* — Christopher D Koharski
*Assistant Examiner* — Nadia A Mahmood

(57) ABSTRACT

An electro-acupuncture device for controlling over active bladder is described. The device includes a housing, circuitry for generating electro-acupuncture stimulus disposed within the housing, and at least one strap for securing the housing to the ankle. The device also includes a pair of D-shaped electrodes received within the bottom outer surface of the housing. The housing of the device is flexible with a low profile and is shaped so that it is conformal to a person's ankle. When the device is strapped to a patient's ankle, the electrodes contact the ankle and provide electric stimulation to the tibial nerve within the ankle.

20 Claims, 11 Drawing Sheets

APPARATUS FOR TRANSCUTANEOUS ELECTRICAL STIMULATION OF THE TIBIAL NERVE

CROSS-REFERENCE TO RELATED APPLICATIONS

This application claims priority from U.S. Provisional Patent Application Ser. No. 61/762,825, filed Feb. 8, 2013.

FIELD OF THE INVENTION

The devices described below relate to the field of electro-acupuncture and non-invasive stimulation of nerves.

BACKGROUND OF THE INVENTION

The peripheral nervous system of a human body consists of the nerves and ganglia outside of the brain and spinal cord. Its main function is to connect the central nervous system to the limbs and organs. Unlike the central nervous system, the peripheral nervous system is not protected by the bone of the spine and the skull, or by the blood-brain barrier, leaving it available for non-invasive, peripheral, electrical nerve stimulation.

Nerves may suffer functional defects due to normal wear and tear, physical injuries, infection, and/or the failure of blood vessels surrounding the nerves. Other defects occur with the inappropriate activation or inhibition of somatic and autonomic pathways. These functional defects may be accompanied by pain, numbness, weakness, and in some cases, paralysis. In other cases, defects may cause undesirable initiation or suppression of physiological functions such as muscle contraction. Problems may include urinary or fecal incontinence. For example, with urinary incontinence, daily physical activities such as laughing, coughing, and sneezing may result in involuntary urination. Similarly, inappropriate contraction and relaxation of muscles that control bladder functioning may result in unplanned and undesired urination.

OAB is a urological condition defined by a set of symptoms that include urgency, with or without urge incontinence, and is usually accompanied by frequency and nocturia. Frequency is defined as urinating more than 8 times a day. In people with OAB, the layered, smooth muscle that surrounds the bladder (detrusor muscle) contracts spastically, sometimes without a known cause, which results in sustained, high bladder pressure and the urgent need to urinate. Normally, the detrusor muscle contracts and relaxes in response to the volume of urine in the bladder and the initiation of urination. People with OAB often experience urgency at inconvenient and unpredictable times and sometimes lose control before reaching a restroom.

Accordingly, urge incontinence and overactive bladder interfere with work, daily routine, and the like; causes embarrassment; and can diminish self-esteem and quality of life.

There are a variety of treatment options for OAB. Conservative treatment starts with bladder training techniques, such as education, timed voiding, restriction of fluid intake, and distraction/relaxation. These can be combined with pelvic floor training exercises that are intended to strengthen and support the pelvic floor muscles. A number of medications are effective for treating OAB. Anticholinergic (antimuscarinic) agents and agents with mixed anticholinergic and bladder wall effects are widely prescribed for OAB. Numerous randomized, controlled trials and systematic reviews have established that these drugs have efficacy over placebo, but the magnitude of benefit in reducing OAB symptoms is modest; a substantial number of patients will not achieve adequate symptom relief, and there are relatively high rates of adverse effects. For patients with OAB refractory to standard treatments, more invasive treatment options are available, such as intravesicular administration of botulinum toxin A, sacral nerve stimulation, or augmentation cytoplasty.

Another technique for overcoming the urge incontinence or OAB involves stimulating either the sacral or tibial nerve by using an electric or magnetic impulse. This is commonly referred to as transcutaneous or percutaneous nerve stimulation. One such electro-medical device capable of providing the required stimuli is commonly referred to as an implantable Pulse Generator (IPG). An IPG typically includes one or more electrodes, an electrical pulse generator, a battery, and a housing. The electrical pulse generator generates a waveform having a specific shape, form, and frequency range capable of stimulating a target nerve. When the electrodes receive the waveform from the generator, they draw energy from the battery and generate an electric field of suitable strength to stimulate the target nerve.

IPGs are typically used for stimulating the sacral nerve and have proven to be somewhat effective. One of the problems associated with IPGs, however, is that implanting the device is invasive, and may cause undesirable complications during and after implantation. Documented complications associated with the implantation procedure include bleeding, infection, or tissue damage. Documented complications after the implantation procedure include generator and/or lead failures. Sometimes a complication may require removal of the device, and re-implantation of a new device.

Another technique commonly used to provide the required impulse is electro-acupuncture nerve stimulation. Electro-acupuncture nerve stimulation involves passing a small electric current between pairs of acupuncture needles. The needles may provide electrical nerve stimulation percutaneously or subcutaneously. Both approaches involve inserting needles (also called the electrodes) into the prescribed acupuncture or trigger points so that the external parts of the needles can be secured against the skin of the patient. Both approaches require the patient to go to a clinic for clinician insertion of the needles into the skin. Additionally, patients have been known to experience some discomfort with these approaches. Furthermore, the known device exhibits some difficulty in use and precision control of the procedure because it is impossible to change a position of the inserted electrode in the body without compromising needle sterility or without removing the whole electrical assembly.

Posterior tibial nerve stimulation (PTNS) is the least invasive form of neuromodulation used to treat OAB and the associated symptoms of urinary urgency, urinary frequency and urge incontinence. PTNS is a type of neuromodulation therapy that uses electrical stimulation to target specific nerves in the sacral plexus that control bladder function. Specifically, tibial nerve stimulation targets the nerves of the pelvic floor with gentle electrical impulses to alter the activity of the bladder. The treatment targets the sacral plexus from an accessible minimally invasive entry point into the nervous system. These urinary symptoms may also occur with interstitial cystitis and following a post-radical prostatectomy. Outside the United States, PTNS is also used to treat fecal incontinence. PTNS has been shown to be effective as a primary therapy. However, treatment for Overactive Bladder and Fecal Incontinence many times begins with conservative therapies including pharmacology. Nearly 80% of patients discontinue use of drugs within the first year, many due to adverse side-effects. Neuromodulation is emerging as an effective modality to treat patients who are not successful with pharmacologic methods.

Since the introduction of PTNS, many published studies have demonstrated PTNS efficacy in treating OAB symptoms. Ridout et al. in *W. J. Obstet Gynaecol* 2010; 30(2) published a literature review evaluating evidence of PTNS for overactive bladder syndrome. The authors found that PTNS may have a role as a useful, minimally invasive treatment option in medically refractory OABS with a 60-81% response rate. However, there is insufficient data to advocate PTNS as a first-line treatment due to its cost and long-term treatment regimen. This invention addresses the cost and treatment method by providing an alternative means of stimulation without breaking the skin.

In 2010, Peters et al. in the *Journal of Urology* Vol. 183 published results of a randomized clinical trial (RCT) comparing PTNS with sham treatment in patients with OABS. Two hundred and twenty (220) adults with OABS were randomized 1:1 to 12 weeks of treatment with weekly PTNS or sham therapy. Overactive bladder and QOL questionnaires, as well as 3-day voiding diaries were completed at baseline and at 13 weeks. Subject global response assessments were completed at week 13. Results showed PTNS subjects had statistically significant improvement in bladder symptoms with 54.5% reporting moderately or markedly improved responses compared to 20.9% of sham subjects from baseline ($p<0.001$). Voiding diary measures after 12 weeks found PTNS subjects had significant improvements in frequency, nighttime voids, voids with moderate to severe urgency and urinary urge incontinence episodes compared to sham. Based on the results, researchers concluded PTNS is safe and effective in treating overactive bladder symptoms.

MacDiarmid et al. in the *Journal of Urology* Vol. 183 described the results of the second phase of a study of PTNS for OAB. The initial study period was 12 weeks. Thirty-two subjects completed 6 additional months of PTNS therapy and 25 completed the full 12 months. Outcome measures included voiding diary data, overactive bladder questionnaires, global response assessments and safety assessments. Patients received an average of 12.1 treatments during an average of 263 days, with a mean of 21 days between treatments. Global response assessments showed sustained improvement from 12 weeks at 6 and 12 months, with 94% and 96% of responders, respectively. The authors found the statistically significant improvements at 12 weeks demonstrated excellent durability through 12 months.

The present invention addresses the issues of the prior art by treating urge incontinence or OAB using a transcutaneous electrical nerve stimulation device. A method is provided for same.

The current accepted form of providing nerve stimulation is a minimally invasive procedure via an office based implantation of a stimulation device. Typically, PTNS is a 30 minute office based treatment via a needle electrode inserted near the tibial nerve, which carries electric impulses from a hand-held stimulator to the sacral plexus. Even though the therapy can be clinically effective with few side effects, the current invasive means of administration causes it to be expensive mainly due to requiring weekly visits for administration by a trained professional. Furthermore, as discussed earlier, difficulty in use and precision control of the therapy delivery device and some patient discomfort have been known.

The posterior tibial nerve is a mixed sensory and motor nerve containing fibers originating from the lumbar and sacral areas of the spine. The sacral nerves modulate the somatic and autonomic nerve supply to the bladder and urinary sphincter. The idea of stimulating the tibial nerve was based on the traditional Chinese practice of using acupuncture points over the common peroneal or posterior tibial nerves to affect bladder activity. The posterior tibial nerve projects to the sacral spinal cord in the same area where bladder projections are found. These are the areas where the therapeutic effect of neuromodulation of the bladder through posterior tibial nerve stimulation takes place. Even though the exact mechanism of action of neuromodulation is unclear, the potential benefit of percutaneous or transcutaneous posterior tibial nerve stimulation is that it may achieve the same neuromodulatory effect as sacral nerve stimulation through a less invasive route.

The present invention provides a safe, reliable, efficacious and convenient means for treating the condition known as urge incontinence or OAB. As discussed in the previous section, transcutaneous electrical nerve stimulation is a proven therapy. This invention packages this for patient convenience, and is essentially painless and simple to use. Most importantly, the device is non-invasive. The device may be strapped (or otherwise adhered) around or on the ankle, or anywhere along the leg wherein the tibial nerve may be electrically stimulated transcutaneously. The device remains in place as the patient ambulates about and outside of the home. Additionally, the patient may secure the device in place without clinician or clinic assistance. This allows the patient with this condition to benefit from the device in the comfort of his/her own home.

The non-invasive nature of the invention further makes it simple to use and does not require administration by a trained professional, in contrast to other minimally invasive devices on the market. The non-invasive nature also means that administration can be performed without requiring the patient to come into a clinic. This reduces the overall cost of therapy and makes it accessible to a much larger population who may have previously been unable to afford a required weekly minimally invasive PTNS procedure. The device conforms to the contours of the region around the ankle of the foot to ensure a low impedance electrical conduit between the electrodes and the skin. This is important to ensure maximum stimulation.

Electro-acupuncture or nerve stimulation devices have been proven effective for the control of nausea and vomiting. An example of an electro-acupuncture device is described in U.S. Pat. No. 4,981,146 to Bertolucci, marketed under the trademark Relief-Band®, for control of nausea and vomiting, is worn on the wrist like a wristwatch, with a watch-like housing which is positioned on the underside or planar surface of the wrist. A patient suffering from nausea or vomiting (from motion sickness, morning sickness, chemotherapy, or anesthesia) can strap the device onto their wrist and turn it on. When turned on, the device emits an electrical stimulation pulse over the P6 acupuncture point (corresponding to the superficial course of the median nerve through the wrist). Within several minutes, most patients experience a substantial relief of nausea. Accordingly, there is a need for non-invasive nerve stimulation devices whereby electricity is passed through electrodes to stimulate nerves strategically located within the body, such as a foot or a leg, for electro-acupuncture or acupuncture treatment of urination related maladies, including non-limiting examples such as overactive bladder or incontinence. However, the anatomical structure of the ankle, within which the tibial nerve is positioned, is quite unique and different from that of the wrist. Unlike the wrist, the ankle comprises a boney projection called the malleous which protrudes outwardly from both the lateral and medial sides of the ankle. In addition, the unique bone, ligament and tendon structure of the ankle make adherence of a device difficult. In particular, the area of depression located between the Achilles tendon and the calcaneus bone in addition to the boney malleous boney projection of the ankle make it particularly difficult to adhere a device to the exterior surface of the ankle so that effective stimulation of the tibial nerve can be achieved. Therefore, what is needed is a non-invasive transcutaneous nerve stimulation device that is conformal to the unique geometry and contours of the ankle region so that effective stimulation of the tibial nerve in treating over active bladder can be achieved.

SUMMARY OF THE INVENTION

The devices and methods described below provide a non-invasive nerve stimulation or electro-acupuncture device, which may be used without the application of conductivity gel, or with minimal application of conductivity gel. The nerve stimulation device comprises a housing preferably shaped like a watch having a housing structure that is conformal to the anatomical structure of the ankle so that the device can be strapped and contactable to a patient's ankle about the tibial nerve. For the purpose of this invention, "watch-like" is defined as having a form and structure comprising a housing, electrodes, a power source and circuitry that can be worn somewhere on the body, may be conformal to the body shape to which is it being attached, further attached to a complementary structure such as a strap, adhesive, stretchable adhesive, elastomeric film and the like for fastening somewhere on a body, or carried within a parcel such as a pocket, glove, sock and the like for locating and affixing somewhere on a body. The housing is designed to be preferably positioned on the ankle. In one embodiment, the device comprises a curved underside specifically designed and dimensioned to fit and conform to the area posterior or behind the malleolus, or the bony prominence, of the ankle. The malleolus is present either on the lateral (outer) or the medial (inner) side of the ankle.

In another embodiment, the housing is constructed such that it is flexible and can conform to the shape of the ankle, in particular, behind the malleolus. In a preferred embodiment, the housing has a low profile having a relatively thin thickness that increases the flexibility of the housing. In addition, the device may comprise a beveled edge to ensure conformity to the curvature of the ankle. Furthermore, the housing may be composed of a material that provides increased flexibility such that the device adheres to the skin of the ankle.

The housing also encloses a control circuitry and a power source, such as an electrochemical cell, that powers the device and provides electrical power for nerve stimulation. The nerve stimulation device includes electrodes for nerve stimulation. In a preferred embodiment, the device preferably includes at least one D-shaped electrode connected to the control circuitry and the power source. A pair of electrodes is preferably positioned within respective openings that extend through the curved sidewall of the bottom surface of the housing of the device. Thus, by positioning the electrodes within apertures of the bottom curved portion of the housing, a greater amount of the external surface area of the electrodes is in direct contact with the curved surface of the ankle region and positioned over the tibial nerve. As the external surfaces of the electrodes are in alignment with the contours of the ankle, more direct contact of the electrode surface with the skin can be achieved when the housing is worn on the patient's ankle. A pair of D-shaped electrodes effectively provides electrical stimulation to the tibial nerve of a patient.

The nerve stimulation device may also comprise a gasket made of an electrically non-conductive material such as neoprene or silicone. The gasket includes two gasket apertures sized and shaped to receive the electrodes when the gasket is applied to the device. The gasket provides electrical insulation between the electrodes so as to prevent a short circuit between the electrodes. The gasket also acts as a seal between the electrodes and the patient's ankle to seal in conductivity gel or other conductive material. It will also serve to retain perspiration in amounts sufficient that the perspiration itself serves as the conductive material.

DETAILED DESCRIPTION OF THE INVENTION

Figure 1:
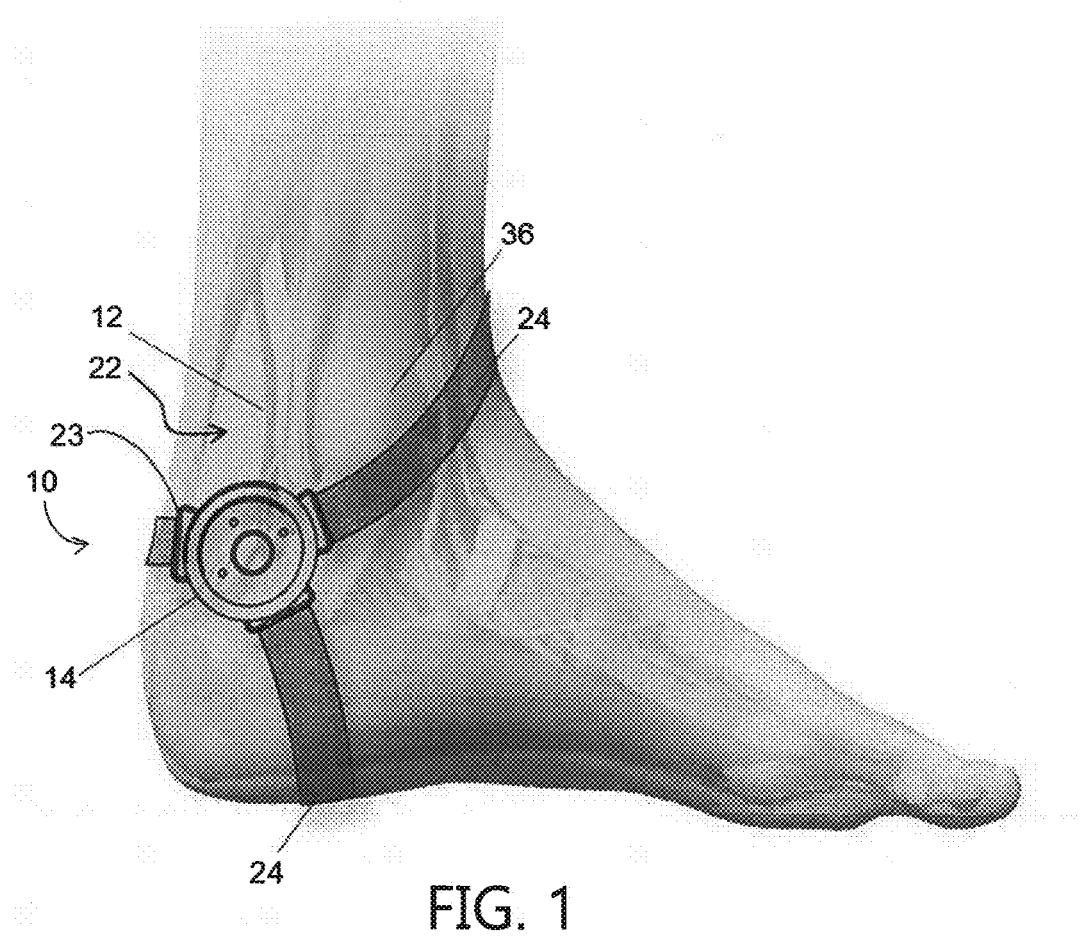
FIG. 1 illustrates an embodiment of the nerve stimulation device of the present invention adhered to an ankle of a human.

Now turning to the figures, FIGS. 1, 3-5, 5A and 6-8 illustrate embodiments of an electro-acupuncture or non-invasive nerve stimulation device 10 of the present invention. In a preferred embodiment, the device 10 is positionable on an ankle 12 of a patient. As illustrated, the device 10 comprises a housing 14, which encloses a pulse generator circuit 16 that controls the operation of the device 10. In addition, a power source 18, such as an electrochemical cell, is positioned within the housing 14 and is electrically connected to the pulse generator circuit 16 (FIG. 9). The electrochemical cell 18 provides electrical power to the device 10 as well as provides a power source for electrical stimulation of a nerve. The device 10 also comprises at least one electrode that is configured to be contactable to the skin of a human and facilitate electrical stimulation. As illustrated, the device 10 preferably comprises two electrodes 20A, 20B that extend through respective openings of the sidewall of the housing 14 of the device 10.

Figure 2:
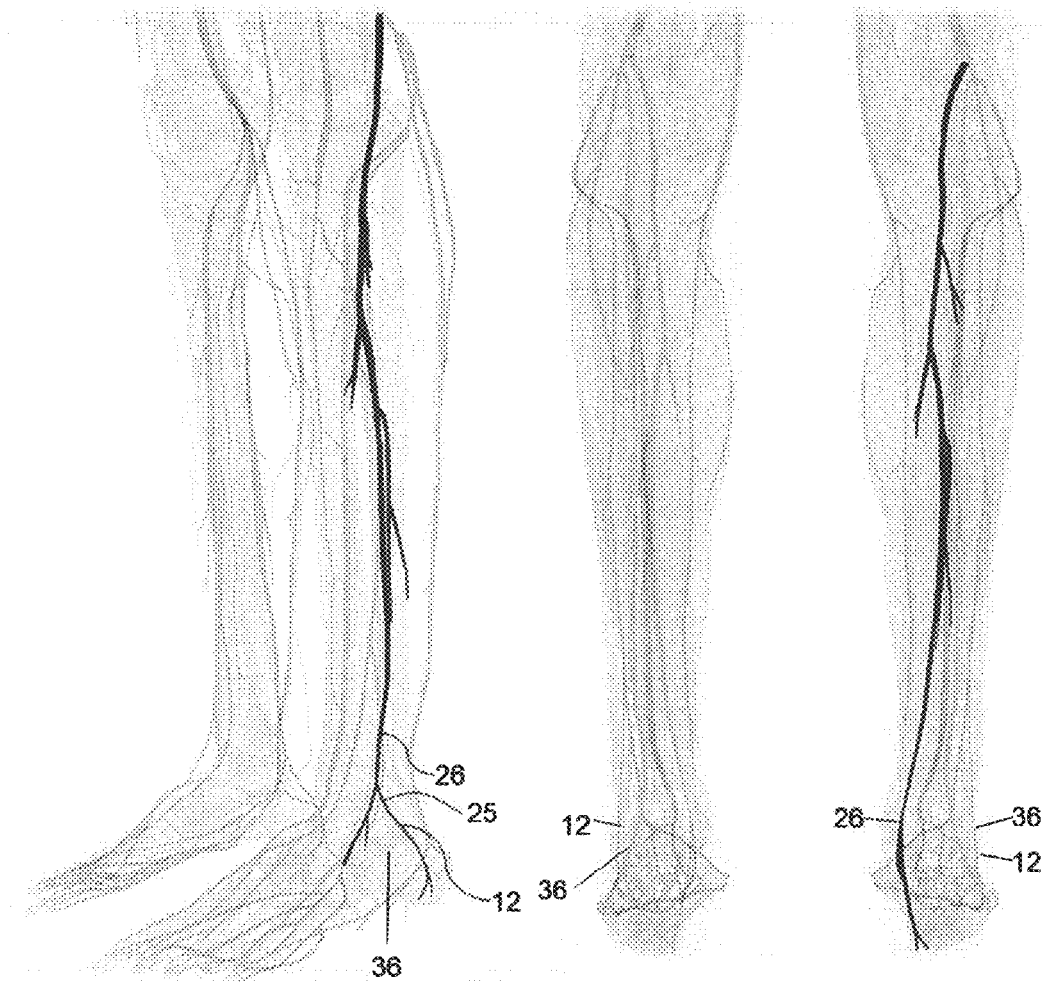
FIG. 2 is a diagram of the human leg illustrating the position of the tibial nerve within the ankle region.

As shown in FIG. 1, the nerve stimulation device 10 is preferably secured to an exterior surface 22 of the ankle 12. In a preferred embodiment, the device 10 comprises at least one strap 24 that secures the device 10 around the ankle 12 such that the at least one electrode 20A, 20B is disposed over the tibial nerve 26 (indicated by the phantom line shown in FIG. 2) and in contact with the skin. As illustrated in FIG. 1, three straps 24 are shown that secure the device 10 to the ankle 12. In a preferred embodiment, each of the straps 24 is positioned through a loop 23 that protrudes from an exterior surface of the housing 14. The loops fasten each of the straps 24 to the device 10. The three-strap embodiment shown in FIG. 1 more firmly secures the device 10 to the ankle 12, which prevents or minimizes dislodgement, displacement or disengagement of the device from the intended target area, i.e., the ankle. It is noted that stimulation of the posterior portion 25 of the tibial nerve 26 (FIG. 2) is a preferred area of nerve simulation in the treatment of overactive bladder. The posterior portion 25 of the tibial nerve 26 is positioned on the lateral side of the ankle 12 and, as such, a preferred location of the device 10 is on the lateral side of the ankle 12 as shown in FIG. 1. Relative to the ankle, electrode 20A is a distal electrode, located distally of proximal electrode 20B, so that the electrodes are arranged along the tibial nerve, with their respective major axes A-A, B-B aligned with the tibial nerve 26 so that sufficient electrical power may be transmitted from the electrode 20A, 20B through the skin to therapeutically transmit a stimulation signal to the tibial nerve 26. Furthermore, receipt of the signal by the nerve results in a positive response in managing urination anomalies like overactive bladder, incontinence and the like. In an embodiment, the respective major axes A-A, B-B of the electrodes 20A, 20B may be positioned parallel to, or alternatively, positioned perpendicular to the tibial nerve 26. The electrodes 20A, 20B are operably connected to the pulse generator circuit 16 within the housing 14. During operation, the pulse generator circuit 16 provides electrical stimulation pulses to the electrodes 20A, 20B, and these pulses are transmitted through the patient's skin to underlying nerves. The strap 24 can be provided in the form of a typical non-elastic watchband, a watchband that includes a segment of elastic material, or it my be comprised of elastic hook and loop fastener material.

Figure 3:
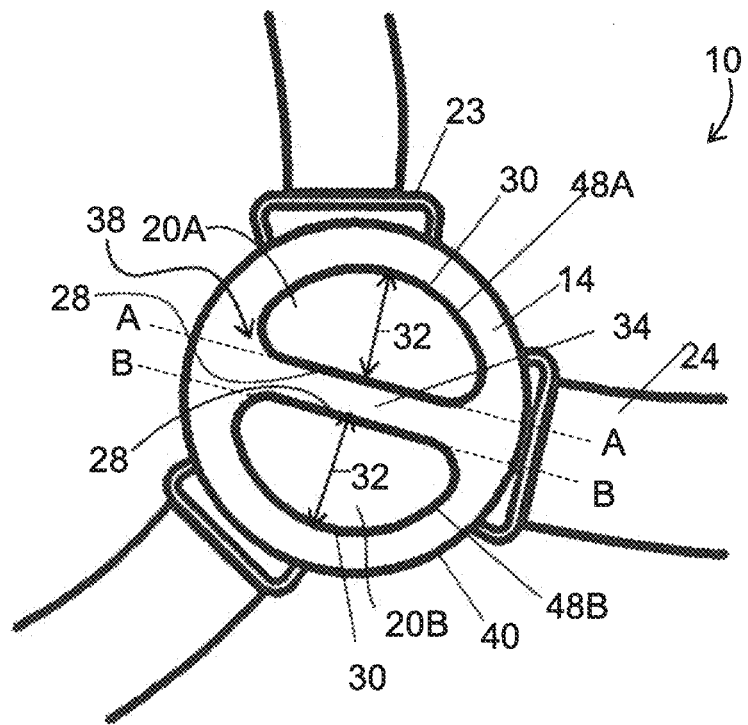
FIG. 3 is a bottom view of the nerve stimulation device shown in FIG. 1.

FIG. 3 illustrates a bottom view of the nerve stimulation device 10. The electrodes 20A, 20B preferably have a "D" or semi-circular shape so that the electrodes define straight edges 28 and radial or arcuate edges 30, and are arranged with the straight edges 28, major axes A-A and B-B, facing each other in opposition. The electrodes have a radius 32 of about 0.5 inches, but may be provided in sizes ranging from 0.25 inches to 1.5 inches (about 0.75 to 4 cm). This radius corresponds to the radius of the arcuate edge 30 in the case where the electrodes are D-shaped, as shown. The electrodes 20A, 20B however, may be more rectangular, each with a width of about 0.5 inches (13 mm) and any radius of curvature which will fit on the chosen housing. The major axis of the electrodes (corresponding to the straight edge 28 of the electrodes, and lying transverse to the ankle during use) may be limited in size in order to conform to the local anatomy of the ankle, so that it may span the tibial nerve 26. The distal to proximal width of the electrode array is limited in size so that the electrodes span a suitable length of the superficial course of the tibial nerve, but do not overlie more distal and proximal nerves.

The electrodes 20A, 20B are separated from each other so that there is an inter-electrode gap 34 along the opposing straight edges of the electrodes. The inter-electrode gap 34 separates the electrodes to prevent a short circuit between the electrodes and force current flow between the electrodes to flow through the body. The inter-electrode gap 34 is approximately 0.14 inches wide (3-5 mm), and may range from 0.05 to 0.5 (1-15 mm) in width. The electrodes 20A, 20B can be manufactured to the appropriate size and shape by stamping, wherein a sheet of suitable metal is stamped by a die having the electrode shape.

The dimensions of the D-shaped electrodes 20A, 20B enhance the effectiveness of the nerve stimulation device 10. The D-shape electrodes 20A, 20B are relatively larger in surface area than conventional electrodes, one example being rounded rectangular or hot-dog shaped electrodes. When an equivalent electric current is supplied to the D-shaped electrode and the smaller conventional electrodes, a lower current density is expected in the larger D-shaped electrodes. A lower current density should result in less effective nerve stimulation with our currently preferred power level (about 10-60 milliamps peak pulse height). The D-shaped electrodes have a larger surface area than the smaller conventional electrodes and provide improved current density and improved nerve stimulation. The improvement is sufficient to allow use of these electrodes without a conductivity gel, or, concomitantly, use of the electrodes with conductivity gel but with much lower applied power. It is not necessary to increase the power level to the D-shape electrodes to maintain our desired current density. In addition, an external surface 35 of the electrodes 20A, 20B, which is contactable to the skin of the ankle 12, may comprise an electrically conductive material. In a preferred embodiment, the external surface 35 of the electrodes 20A, 20B may comprise copper, gold, platinum, an electrically conductive alloy or combination thereof. The external surface 35 of the electrodes 20A, 20B may be composed of these materials or, alternatively, may comprise a coating of these materials. Additional embodiments of the electrodes 20A, 20B are disclosed in U.S. Pat. No. 6,735,480 to Giuntoli et al., which is assigned to the assignee of the present invention and incorporated herein by reference.

In a preferred embodiment, the size and shape of the housing 14 are substantially determined by: (1) the need to fit comfortably on the ankle 12, (2) the ability to allow free extension and flexion of the ankle 12, (3) the capability of concentrating stimulation over a nerve, in this case the tibial nerve 26 positioned within the ankle 12, and (4) the capacity to be therapeutic. In addition, the proper fit and conformity of the device 10 to the body also minimize energy loss and ensure more of the electrical energy reaches the intended nerve. For example, the housing is dimensioned to provide effective transcutaneous stimulation for efficacious therapy of overactive bladder. The better the fit and conformity of the device 10 to the ankle 12, the more depth penetration of the electrical stimulation to the nerve is achieved, and thus an improved therapeutic stimulation results. In addition, material selection of the composition of the housing 14 is also important to provide a correct fit of the device 10 to the exterior surface of the body, particularly the ankle 12 which is more complex in structure, and, in some cases, uniquely convoluted for certain individuals, in comparison with previous transcutaneous devices such as wrist stimulators which tend to be positioned on a planar surface of the wrist. In an embodiment, the housing 14 is constructed such that it is conformal to the contours of the ankle 12. As previously mentioned, the unique structural features of the ankle 12, particularly the boney bump of the lateral malleolus 36 (FIGS. 1 and 2) that protrudes outwardly on the lateral side of the ankle 12, make device fit and conformity particularly difficult. Furthermore, the medial side of the ankle 12 also comprises a boney malleolus which protrudes outwardly from the ankle 12 which also adds to the difficulties of device fit and conformity. Optimal fit and conformity of the device 10 to the intended area, i.e. the ankle 12, is critical in achieving adequate penetration depth of the electrical stimulation to the targeted nerve, i.e. the tibial nerve 26, within the body so that optimal treatment and symptom relief can be provided. In certain cases wherein the configuration and structure of the intended area are unique either by origin, accident or defect, a mold of the target site may be created and then used to fabricate a customized housing. In addition, conductive gels, adhesives, pastes and the like may also be used to facilitate improved contact with the skin.

Since the device 10 is preferably positioned on the lateral side of the ankle 12 to stimulate the posterior portion of the tibial nerve 26, the boney lateral malleolus 36, in addition to the radius of curvature of the ankle 12, tendons, and ligaments make it difficult to properly position the device such that it is in contact with the skin of the ankle. Because of the unique shape of the ankle 12, the housing 14 is designed to comprise a contoured curved bottom surface 38 that is conformally positionable adjacent the lateral malleolus 36 and the posterior portion 25 of the tibial nerve 26. In addition, the housing 14 may be designed to be positionable within the depression formed between the calcaneus bone and the Achilles tendon of the ankle 12.

Figure 4:
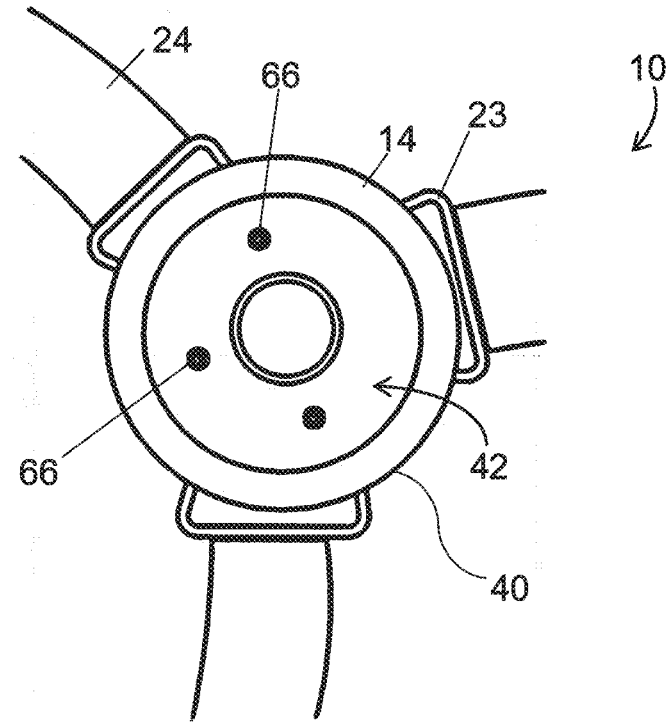
FIG. 4 is a top view of the nerve stimulation device shown in FIG. 1.
Figure 5:
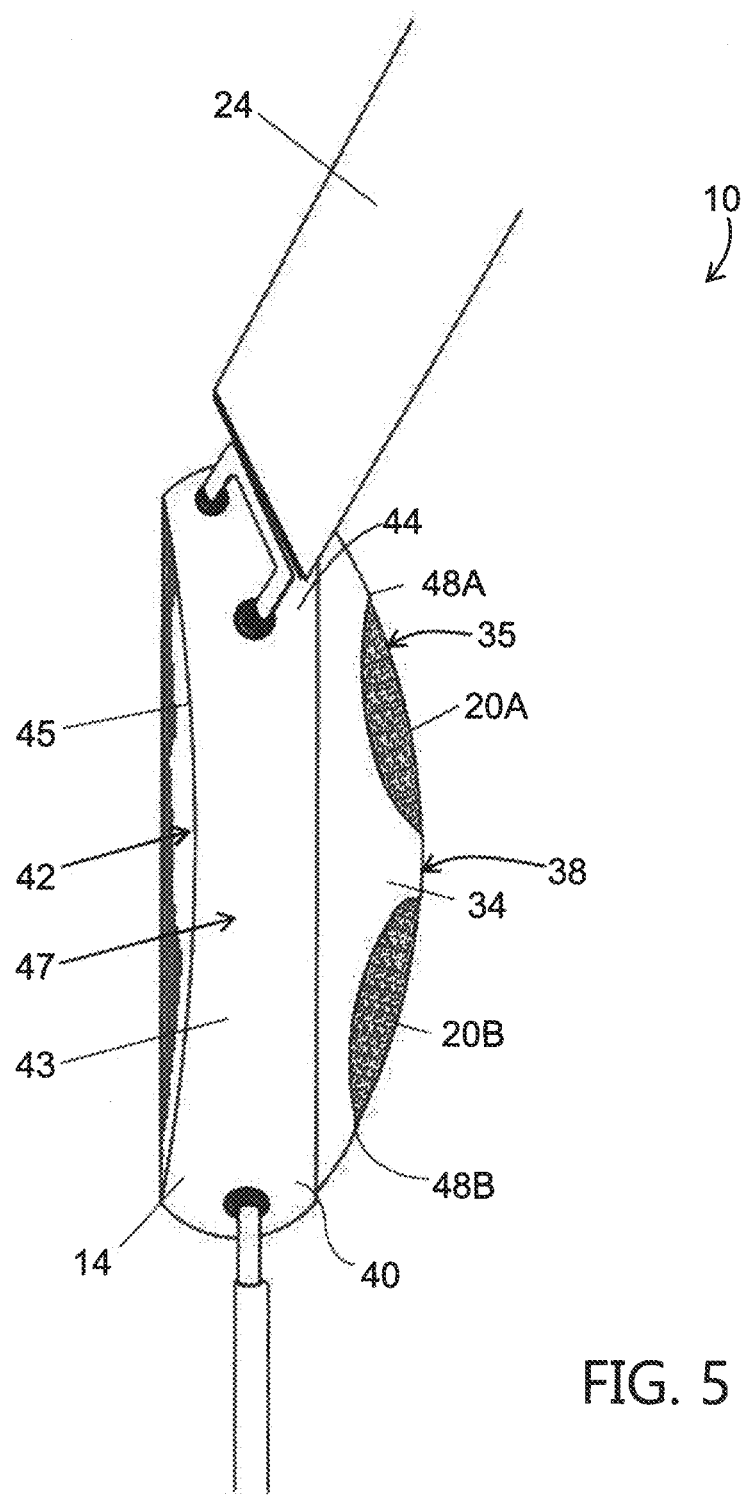
FIG. 5 illustrates a side view of the nerve stimulation device of FIG. 1.
Figure 5A:
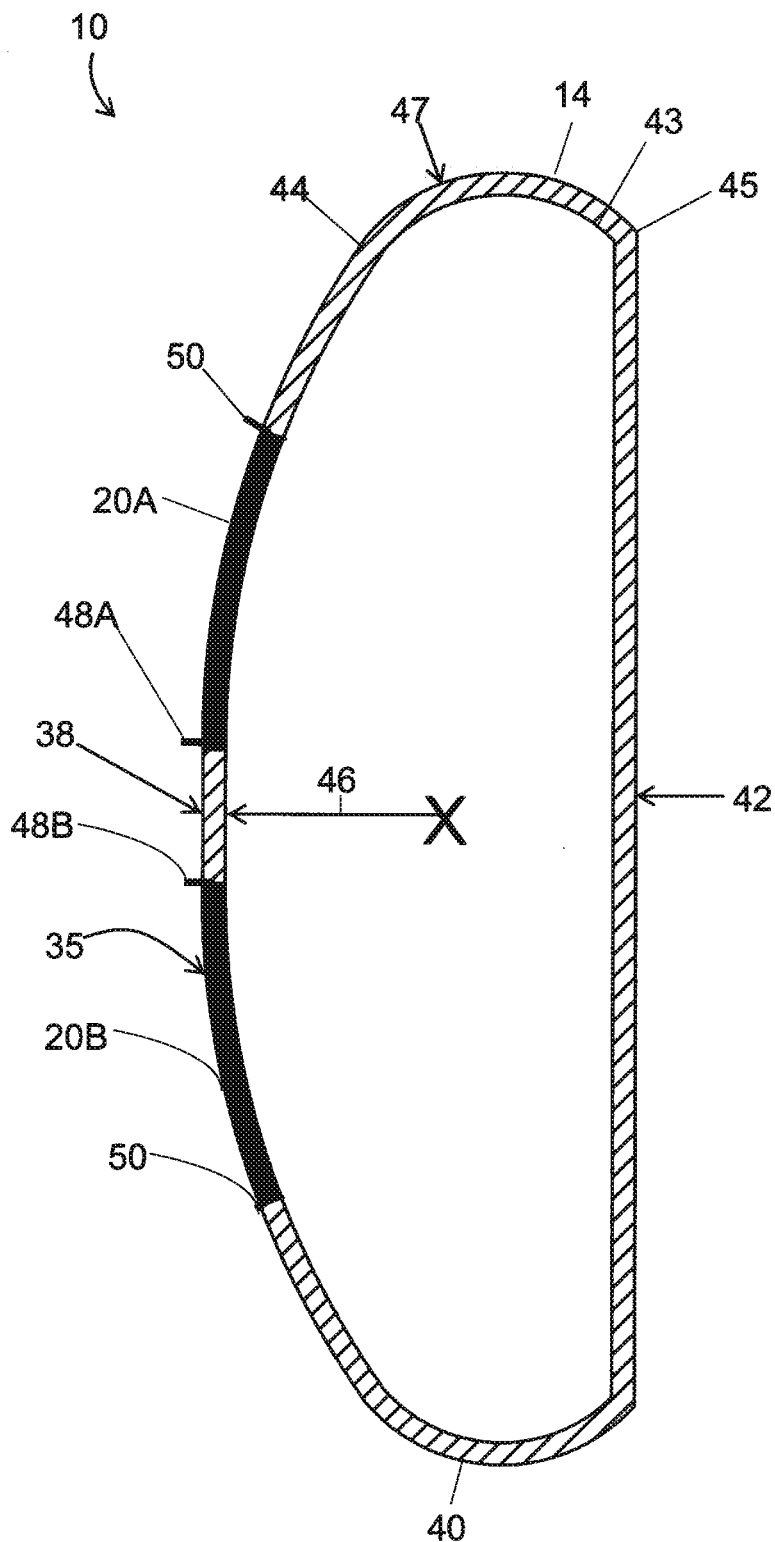
FIG. 5A is a cross-sectional side view of the nerve stimulation device shown in FIG. 5.

In a preferred embodiment, illustrated in FIGS. 3, 4, 5 and 5A, the housing 14 of the device 10 comprises an annular sidewall 40 that provides an exterior housing perimeter. A top surface 42 of the housing 14, illustrated in FIGS. 4, 5, and 5A, extends from an upper portion 43 of the sidewall 40 and the bottom surface 38 of the housing 14 extends from a base portion 44 of the annular sidewall 40 (FIGS. 5 and 5A). In a preferred embodiment, the annular sidewall 40 comprises a beveled exterior surface 47 so that the device 10 is more conformal to the ankle region 12. More specifically, the bottom surface 38 of the housing 14 preferably has a convex shape. In a preferred embodiment, the convex bottom surface 38 has a radius of curvature 46 ranging from about 0.001 inch (0.0025 cm) to about 0.01 inch. (0.025 cm) (FIG. 5A). The curved convex exterior bottom surface 38 of the housing 14 is illustrated in the side and cross-sectional views of FIGS. 5 and 5A respectively. It is this convex exterior bottom surface 38 of the housing 14 of the device 10 that contacts the exterior surface of the skin of a patient. More specifically, it is the convex exterior bottom surface 38 of the housing 14 of the device 10 that contacts the exterior surface of the skin of the ankle 12 adjacent the malleolus 36 of a patient.

In addition, as illustrated in the embodiment shown in FIGS. 4, 5 and 5A, the top surface 42 of the housing 14 is preferably planar. Furthermore, the top surface 42 of the housing 14 may be positioned such that it is recessed from a top edge 45 formed by an end of the upper portion 43 of the sidewall 40 of the housing 14. This recessed feature of the top surface 42 is designed to prevent unintentional contact of the control buttons that are positioned about the top surface 42 of the housing 14.

As mentioned earlier, in a preferred embodiment, the size and shape of the housing 14 may be configured by molding the housing 14 to the specific area of the body to which the device 10 is contactable. For example, the housing 14 may be molded to the ankle 12 of the patient so that a more exacting fit may be achieved. In so doing, the housing 14 of the device 10 may be made of a moldable material examples of which include, but are not limited to a polymeric material such as, silicone rubber, acrylonitrile butadiene styrene (ABS), styrene, polycarbonate, neoprene and combinations thereof.

As shown, the bottom surface 38 of the sidewall of the housing 14 comprises a first aperture 48A and a second aperture 48B through which the respective first and second electrodes 20A, 20B extend therethrough. In an embodiment, the external surfaces 35 of the electrodes 20A, 20B are positioned such that they are flush with the curved bottom surface 38 of the housing 14. Alternatively, the electrodes 20A, 20B may be positioned within the apertures 48A, 48B so that the external surfaces 35 of the respective electrodes 20A, 20B extend a distance away from the bottom surface 38 of the housing 14. Thus, by positioning the electrodes 20A, 20B through the bottom surface 38 of the sidewall 40 of the housing 14, a more conformal fit of the device 10 can be achieved. More specifically, by having the electrodes 20A, 20B reside within respective electrode apertures 48A, 48B, so that the external surface of the electrodes 20A, 20B are about flush with the curved contour of the bottom surface 38 of the housing 14, more surface area of the external surface of the electrodes 20, 20B will be in contact with the skin of the ankle 12. Therefore, by having an increased amount of surface area of the electrodes 20A, 20B in more direct contact with the geometry of the ankle 12, improved nerve stimulation, particularly that of the tibial nerve 26 can be achieved.

In addition, a gasket 50 (FIG. 5A) may be positioned around the perimeter of the electrode 20A, 20B to further secure the electrode within the respective electrode apertures 48A, 48B. In an embodiment, the gasket 50 comprises respective gasket apertures within which electrodes 20A, 20B may be received. The gasket 50 can be made from any suitable dielectric or electrical insulating material such as neoprene, silicone, urethane, rubber or other materials. Thus, the convex shape of the bottom surface 38 of the housing enables a secure fit of the device 10 and the electrodes 20A, 20B to be positioned adjacent the lateral malleolus 36 of the ankle 12. Furthermore, the convex shape of the bottom surface 38 of the housing 14 provides improved contact with the skin of the ankle 12.

Figure 6:
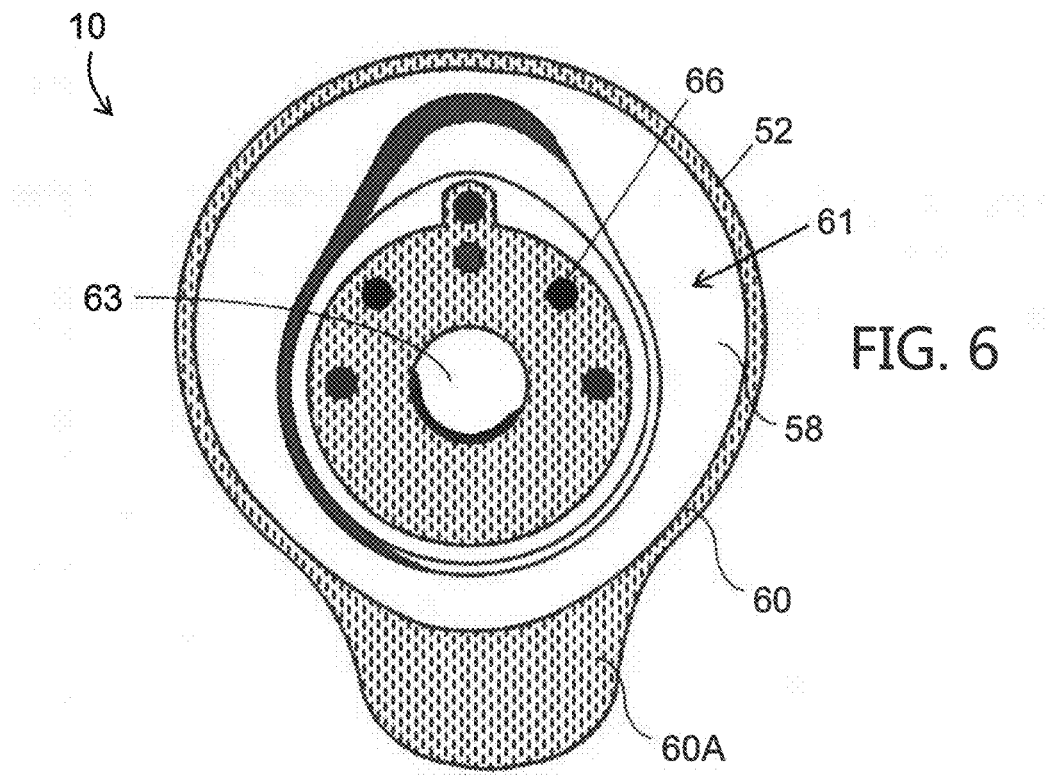
FIG. 6 shows a top view of the nerve stimulation device of the present invention comprising an alternate housing embodiment.
Figure 7:
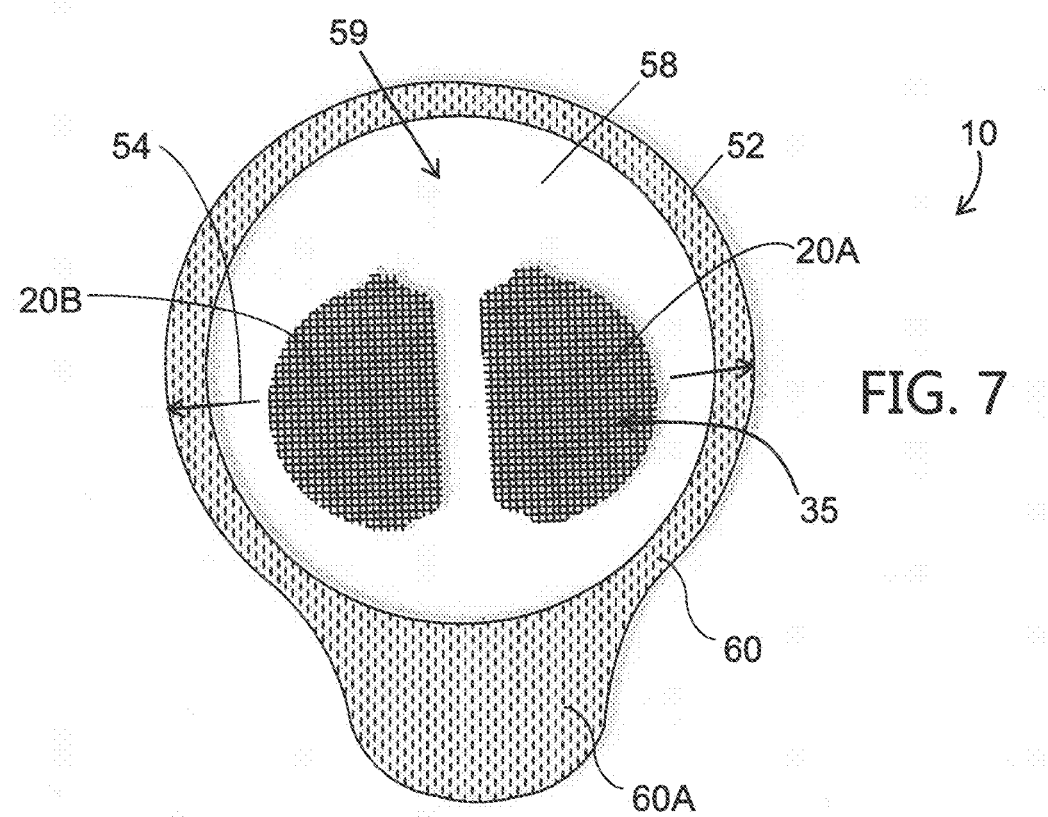
FIG. 7 illustrates a bottom view of the nerve stimulation device of the present invention comprising an alternate housing embodiment.
Figure 8:
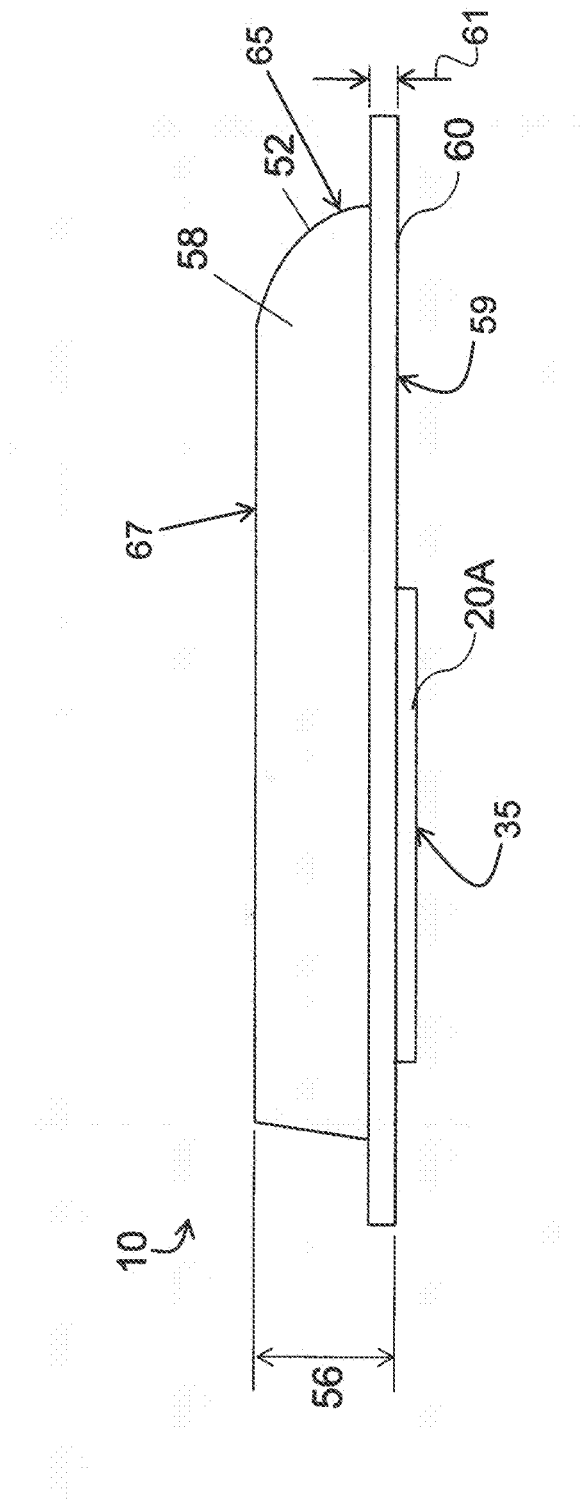
FIG. 8 shows a side view of the nerve stimulation device of the present invention comprising an alternate housing embodiment.
Figure 9:
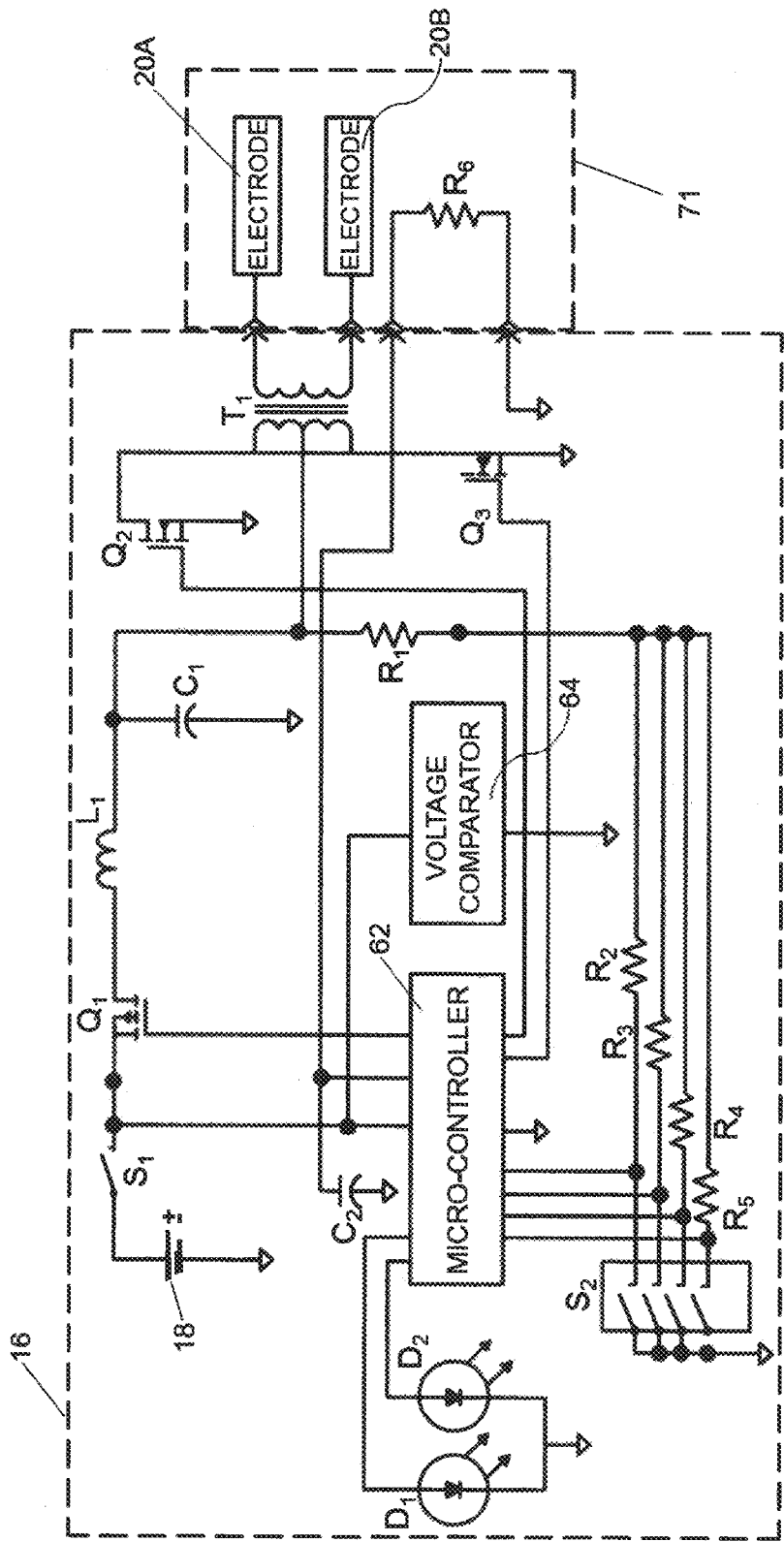
FIG. 9 illustrates an embodiment of an electrical circuit diagram of the pulse generating circuit of the nerve stimulation device of the present invention.

FIGS. 6, 7 and 8 illustrate views of an alternate embodiment of the housing 52 of the nerve stimulation device 10 of the present invention. As illustrated, the alternative housing 52 is of a patch like configuration having a relatively low profile. In a preferred embodiment, the housing 52 has a curved form with a diameter 54 ranging from about 1.0 inch to about 3.0 inch (FIG. 7) and a housing thickness 56 ranging from about 0.25 inch to about 1.0 inch (FIG. 8). This preferred construction of the housing 52 provides increased flexure of the device 10 around curved radius such as the boney malleolus 36 of the ankle 12. In a preferred embodiment, the device 10 has a thickness to diameter ratio ranging from about 1 to about 3 which enables the housing to bend and conform to the curved regions of the ankle 12. In addition, the housing 52 of the device 10 may be composed of a polymeric material which includes, but not limited to, silicone rubber, ABS, styrene, polycarbonate, neoprene and combinations thereof.

FIG. 6 illustrates a top view of the alternate embodiment of the housing 52 and FIG. 7 illustrates a bottom view of the alternative embodiment of the housing 52. As shown, the housing 52 comprises a top housing or center housing portion 58 that extends from a bottom housing portion 60. Similar to the previous housing embodiment 14, the alternative housing embodiment 52, may comprise a recessed top surface 61 to minimize unintentional contact with operational control buttons 63. A tab portion 60A may extend outwardly from the perimeter of the bottom housing portion 60. This tab portion 60A facilitates application and removal of the device 10 from the skin. In a preferred embodiment, the bottom or center portion 60 of the housing 52 may be separatable from the top portion 58 of the housing 52 by pulling tab portion 60A. When separated, the top or center portion 58 of the housing 58 is left behind on the skin. In an embodiment, a bottom surface 59 of the bottom housing portion 60 is contactable to the skin of the ankle 12. In a more preferred embodiment, the electrodes 20, 20B may be positioned within the bottom surface 59 of the center portion 58 of the housing 52 so that the external surfaces 35 of the electrodes 20A, 20B are about flush with the bottom surface 59.

As shown, the top portion 58 preferably comprises a curved perimeter having a beveled exterior surface 65 and top surface 67. In a preferred embodiment, illustrated from the side view shown of FIG. 8, the bottom housing portion 60 comprises an outer perimeter having a relatively thin perimeter depth. In a preferred embodiment, the perimeter depth ranges from about 0.25 inch to about 1.0 inch. This relatively thin depth of the bottom housing portion 60 in addition to the overall relatively thin housing depth 56 increases the flexibility of the device 10. In other words, the relatively thin depth of the housing 52 and of the device 10 increases its ability to bend both in left and right and upward and downward directions.

FIG. 9 provides an embodiment of a detailed circuit diagram of the pulse generator circuit 16. The circuit 16 is powered by a power source 18, such as an electrochemical cell. The cell is selected on the basis of its capacity rating, which defines the maximum number of times that the electrotherapy device will operate. In a preferred embodiment, two CR2025 3 volt lithium coin cell batteries are connected in series (6 volts total battery supply). The average current drawn from the batteries is approximately 0.9 milliamps when delivering therapeutic pulses of 35 milliamps peak pulse amplitude (350 microsecond pulse width at 31 hertz frequency) into a simulated human skin load (500 ohm resistor). This current draw compares well to the maximum direct current draw for this type of battery, which is typically 3 milliamps. The typical battery capacity for the CR2025 is 150 milliampere-hours at a continuous electrical current draw of 0.2 milliamperes. A draw of 1 milliamp should produce somewhat less than 150 hours of battery life.

As shown in the electrical schematic diagram of FIG. 9, the power source 18 is connected through switch $S_1$. Switch $S_1$ is operable by the patient and enables the patient to turn on and off the electrotherapy device. Switch $S_1$ is in the closed position during operation when the patient has turned on the electrotherapy device. During operation, the power source 18 discharges pulses into inductor $L_1$. Inductor $L_1$ controls the delivery of current to capacitor $C_1$ and reduces energy loss to maximize battery efficiency, $C_1$ stores the electric charge and accumulates a corresponding voltage until commanded to discharge the accumulated voltage to transformer $T_1$, whereupon $T_1$ steps up the voltage for output to the patient in the form of therapeutic output pulses. Microcontroller 62 controls the circuit operations. Microcontrollers are typically characterized by their operating voltage range, their electrical current consumption, their operating speed (clock rate), the number of bits used for operations (e.g., 4 bit, 8 bit, 16 bit, etc.), the number of programmable input/output lines, software program storage space, and integrated special functions (e.g., A/D converters, high current source or sink capability, serial communication ports, etc.). Other factors include cost and availability. 4-bit and 8-bit microcontrollers are favored due to their small size, low cost, and low power consumption (e.g., Samsung KS51 series and Toshiba TLCS47 series 4-bit microcontrollers, and Samsung KS86C series, Toshiba TLCS870 series and Microchip 16C5x series 8-bit microcontrollers). A preferred embodiment uses a Microchip 16C54A 8-bit microcontroller.

Switch $S_1$ and microcontroller 62 are connected to transistor $Q_1$, which together with inductor $L_1$ comprise a switched inductor. Microcontroller 62 connects power source 18 to the inductor $L_1$ through transistor $Q_1$, which microcontroller 62 operates as a switch. The microcontroller 62 repeatedly opens and closes transistor $Q_1$ to send discharge pulses to inductor $L_1$. This causes current to flow into inductor $L_1$ and capacitor $C_1$. Inductor $L_1$ causes this current to increase at a controlled rate, thereby causing a voltage to develop across capacitor $C_1$ at a controlled rate, thereby reducing energy losses. When transistor $Q_1$ is opened, the current into inductor $L_1$ begins to decrease. Residual current in inductor $L_1$ is then allowed to flow to capacitor $C_1$, causing its voltage to increase slightly. Once this residual current goes to zero, this causes capacitor $C_1$ to be isolated in the electrical circuit, thereby preserving the voltage stored on it. In an embodiment, resistors $R_1$ through $R_5$ may provide a discharge path for capacitor $C_1$ if any of the switches $S_2$ are closed. These resistors are chosen to be high values to limit the discharge current from $C_1$ to acceptably low values. The value of inductor $L_1$ is preferably chosen to conserve battery life and provide small size and low cost. However, testing has demonstrated that inductor $L_1$ can be replaced by a smaller, lower cost, low value resistor while still obtaining the advantage of regulated output while the battery voltage decreases with use. The drawback of this method is that, while battery life is enhanced vis-a-vis unregulated output, battery life is compromised vis-a-vis the switched inductor embodiment due to energy losses in the resistor.

Inductor $L_1$ is connected to capacitor $C_1$, which is chosen typically to be a high capacitance value to maximize current storage. Current flowing through inductor $L_1$ and into capacitor $C_1$ causes voltage to build across capacitor $C_1$ that is proportional to the amount of current delivered over a particular time period, e.g., the battery discharge time. Microcontroller 62 monitors the charge/voltage built up on the capacitor $C_1$ so it knows when to stop the battery discharge pulses and/or initiate a transformer discharge pulse (therapeutic pulse). Low voltage storage capacitor $C_1$ is connected to $R_1$, which together with switch array $S_2$ and resistors $R_2$ through $R_5$ comprise a voltage divider switching network. Switch array $S_2$ is manipulated by the patient to select one of a number of available "intensity" settings. As shown in FIG. 9, switch array $S_2$ selects one of a number of resistors in a voltage divider array formed by resistor $R_1$ and resistors $R_2$ through $R_5$.

$R_1$ of the voltage divider switching network is preferably connected to voltage comparator 64. Using the voltage comparator 64, the microcontroller 62 monitors the voltage across capacitor $C_1$, and continues to allow voltage to build until the voltage comparator 64 signals that the voltage has reached a predetermined voltage value.

The next step is to send a therapeutic pulse from the low voltage storage capacitor to the transformer. The low voltage storage capacitor is connected to transformer $T_1$. Transformer $T_1$ is chosen to have a voltage step-up characteristic based on the desired therapeutic output requirements and the load connected to the electrodes 20A and 20B. Once voltage across $C_1$ has reached a predetermined value, microcontroller 62 closes either transistor $Q_2$ or $Q_3$ to discharge the capacitor into the transformer $T_1$. This sends the voltage to the output stage to be stepped up by transformer $T_1$. In a preferred embodiment, the transformer has a turns ratio of approximately 20, a low resistance primary winding (approximately 2 ohms), and a high inductance secondary winding (approximately 1 Henry). The turns ratio is selected based on the maximum voltage on the storage capacitor at the primary and the desired maximum voltage delivered to the skin through the electrodes at the secondary, e.g., 3 volts at the primary can deliver 3*20=60 volts at the secondary (other factors such as transformer core saturation must be considered). The low resistance primary is needed for reduced power consumption. The high inductance secondary is needed to achieve a nominally constant current therapeutic output over a range of skin impedance values. Skin impedance changes with time for a particular patient, and can be very different between patients. A nominally constant current output allows a predictable level of therapeutic current to be delivered regardless of patient skin characteristics, thereby providing better therapeutic value.

Transistors $Q_2$ and $Q_3$ are needed to move electrical current through the transformer $T_1$ primary winding in one direction or the other, thereby creating positive or negative therapeutic pulses at the electrodes 20A and 20B. Preferably, the microcontroller 62 alternately operates $Q_2$ and $Q_3$ to provide alternately positive and negative pulses to the electrodes. (Alternating operation of $Q_2$ and $Q_3$, together with a center tap attachment at the center of the transformer winding, creates a polarity switching circuit which creates the alternating positive and negative voltage output from the transformer.) This prevents any iontophoretic or electropheretic effect on the patient's skin. Alternatively, transformer $T_1$ can be replaced by a standard transformer to create single polarity pulses, or it can be removed and the inductor $L_1$ and capacitor $C_1$ chosen to provide the high voltage directly to the electrodes with a different switching means to effect different polarity pulses, if required. The operation of transistor $Q_2$, $Q_3$ and $Q_1$ may be controlled so that the inductor $L_1$ is always disconnected from the power source 18 when the capacitor is discharging into the transformer. In this manner, current is supplied to the transformer only from the capacitor and not from the electrochemical cell 18.

The circuit can also create a display to the patient. Microcontroller 62 may be connected to light emitting diodes (LED) 66 (FIGS. 4 and 6). In a preferred embodiment, a first light emitting diode 66 may comprise a green LED that is flashed at a low duty cycle to conserve battery power and is used to indicate normal operation. A second light emitting diode 66 may comprise a red LED that is flashed at a faster rate than the first LED and is used to indicate the "low battery" warning. Alternative display methods may be used including liquid crystal display, sound, vibration, etc.

In a preferred embodiment, capacitor $C_1$ can be discharged directly into the skin if certain changes are made to the circuit. Specifically, a diode can be placed in series between inductor $L_1$ and capacitor $C_1$, which is then chosen to be a high voltage, high capacitance component, i.e., a standard "boost" regulator configuration. The diode allows a high voltage to be stored on the capacitor from a lower voltage source. Resistor divider values are then chosen to suitably divide the peak high voltage down to a value suitable for the voltage detector.

Furthermore, biphasic pulses can be created using capacitor $C_1$ as an input to a standard H-bridge transistor circuit with suitable transistors, with the electrodes connected to the middle of the H-bridge (the H-bridge is another form of polarity switching circuit). This method is not preferred because power consumption is relatively high, resulting in low battery life, and the therapeutic output becomes nominally constant voltage instead of the preferred nominally constant current achieved using a transformer or tapped inductor. However, where the H-bridge is desirable for other reasons, the battery life may be extended vis-a-vis direct connection to the battery. Additional preferred embodiments of the pulse generator circuit 16 are disclosed in U.S. Pat. Nos. 6,076,018 and 7,217,288, both to Sturman et al., and are assigned to the assignee of the present invention, the contents of which incorporated herein by reference.

Furthermore, as illustrated in the electrical schematic diagram of FIG. 9, the pulse generator circuit 16 may also comprise a smart electrode assembly 71 comprising electrodes 20A, 20B and resistor $R_6$ that is connectable thereto. In this embodiment, the microcontroller 62 and capacitor $C_2$ are used to determine the presence or absence of $R_6$. When the electrode assembly 71 is connected, the resistor $R_6$ forms an RC timing circuit in conjunction with capacitor $C_2$ in the housing 14, 52. In a preferred embodiment, the microcontroller 62 is connected to a parallel RC circuit whose resistance and capacitance are known, therefore, the RC time constant is known. If the electrode assembly 71 is not connected, the resistance value in the RC circuit is infinite and the time constant is quite long. If the electrode assembly 71 is in place, i.e., resistor $R_6$ is in place, the voltage is low; if not, the voltage should still be high (that is, the time constant is long). Thus, the microcontroller 62 can determine the electrical parameter (resistance of $R_6$) by determining the time constant of the RC timing circuit created upon connection of the electrode assembly to the housing 14, 52 and the resultant placement of the resistor $R_6$ into the circuit 16.

Upon determination of the resistance value of $R_6$ or the time constant of the resultant RC timing circuit, the microcontroller 62 then sets the output range according to a predetermined schedule which is programmed into the microcontroller 62. For example, the microcontroller 62 and electrode combination 20A, 20B may be set up so that upon sensing the presence of resistor $R_6$, the microcontroller 62 will produce a pulsed stimulation output in a first predetermined output range, while upon failure to sense resistor $R_6$ within the electrode assembly 71 the microcontroller 62 will produce a pulsed stimulation output in a second predetermined output range. Different values for the resistance of $R_6$ may be used to provide multiple configuration inputs corresponding to multiple output options. For example, one electrode assembly 71 may use a certain resistance providing a shorter first time constant, while a second electrode assembly (not shown) may use a different resistance resulting in a longer second time constant. The microcontroller 26 may then be configured to check the capacitor voltage at the first time constant. If the voltage is still high, then the microcontroller 26 will check again at the second time constant for the presence of the second assembly. The number of different potential values for $R_6$ will depend on the number of desired output options, and the resolution of the microcontroller 26 (its ability to discriminate between sensed time constants). Additional embodiments of RC timing circuits that could be used with the nerve stimulator device 10 of the present invention are disclosed in U.S. Pat. No. 6,076,018 to Sturman et al., assigned to the assignee of the present invention, the contents of which incorporated by reference.

Figure 10B:
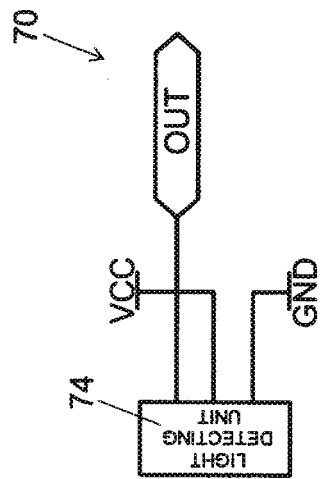
FIG. 10B illustrates an embodiment of an electrical circuit diagram of an infrared remote control receiving device that may be used with the nerve stimulation device of the present invention.
Figure 10A:
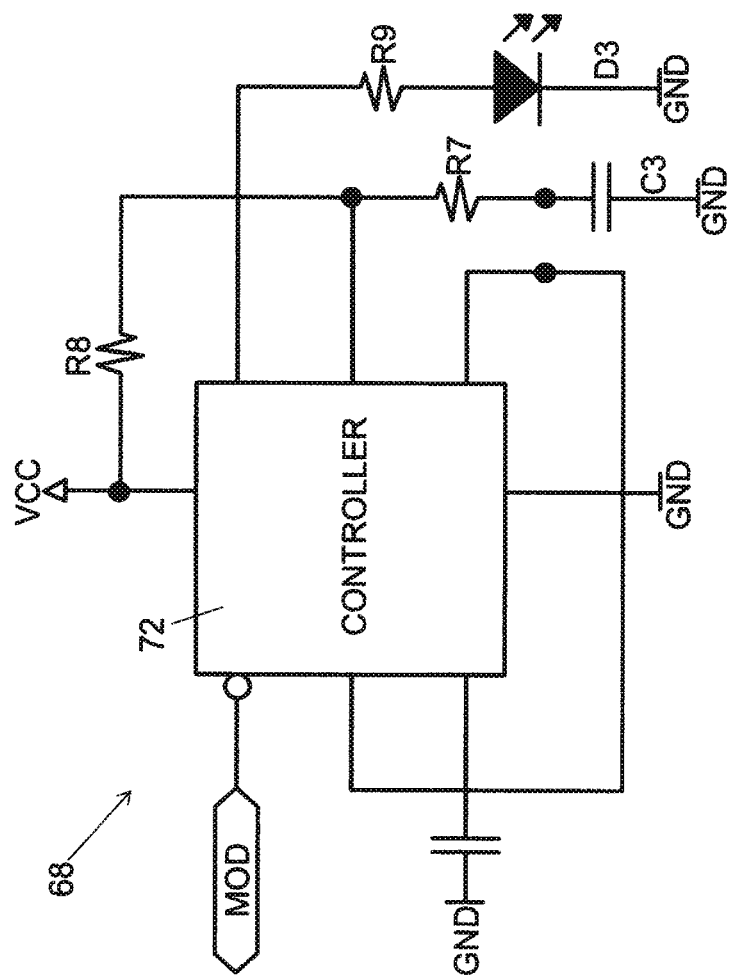
FIG. 10A illustrates an embodiment of an electrical circuit diagram of an infrared remote control transmitting device that may be used with the nerve stimulation device of the present invention.

In addition, operation of the stimulator device 10 may be controlled through the use of a remote control. For example, a remote control operated through infra red (IR), radio frequency (RF) or telemetry could be used to control the operation of the stimulation device 10. An example of a transmitting infrared remote control circuit 68 is given in FIG. 10A. As illustrated, the circuit 68 comprises a controller 72, capacitors $C_3$ and $C_4$, resistors $R_8$-$R_9$ and diode $D_3$ that are electrically connected to transmit an infrared control signal. FIG. 10B illustrates an electrical schematic diagram of an example of an infrared remote control receiving circuit 70. As shown, the circuit 70 comprises a light detecting circuit 74, an electrical power input and a signal output. Such a remote control receiving circuit 70 could be electrically connected to the pulse generator circuit 16. In a preferred embodiment, an output of the infrared remote control receiving circuit 70 could be electrically connected to the micro controller 62.

In use, the user preferably straps the device 10 onto the ankle 12 so that the electrodes 20A, 20B overlie the tibial nerve 26. When applied to the ankle 12, the electrodes 20A, 20B are arranged proximally and distally on the skin of the ankle 12. In a preferred embodiment, the device 10 is attachable so that it is in physical contact with the lateral side of the ankle 12. Alternately, the device 10 could also be attached so that it is in physical contact with the medial side of the ankle 12. As defined herein, "lateral side" is the outside side of the ankle that faces away from the body. The "medial side" is the inside of the ankle that faces towards the opposite leg. The electronics within the housing 14 are activated by the user, and are programmed to generate an electrical pulse pattern. In a preferred embodiment, the electrical pulse pattern may comprise a 350 microsecond pulse width at about 31 pulses per second at power levels of about 10-35 milliamps peak pulse height. In addition, power levels of about 40 milliamps peak pulse height to about 80 milliamps peak pulse height may also be achieved. This pulse pattern is effective to create an electro-acupuncture effect on the nerve, but other pulse patterns may also be effective. Additionally, the user may apply gel, and the device may be programmed to generate pulses at lower power levels to achieve a similar level of stimulation while reducing battery consumption. The user need not be overly precise regarding the placement of the electrodes over the ankle, as the D-shaped electrodes are much less position sensitive than the conventional electrodes used in our prior devices. That is, small variations in the longitudinal and transverse location of the electrodes relative to the tibial nerve in the ankle do not negatively affect the transmission of electrical stimulus from the electrodes to the tibial nerve.

Figure 11A:
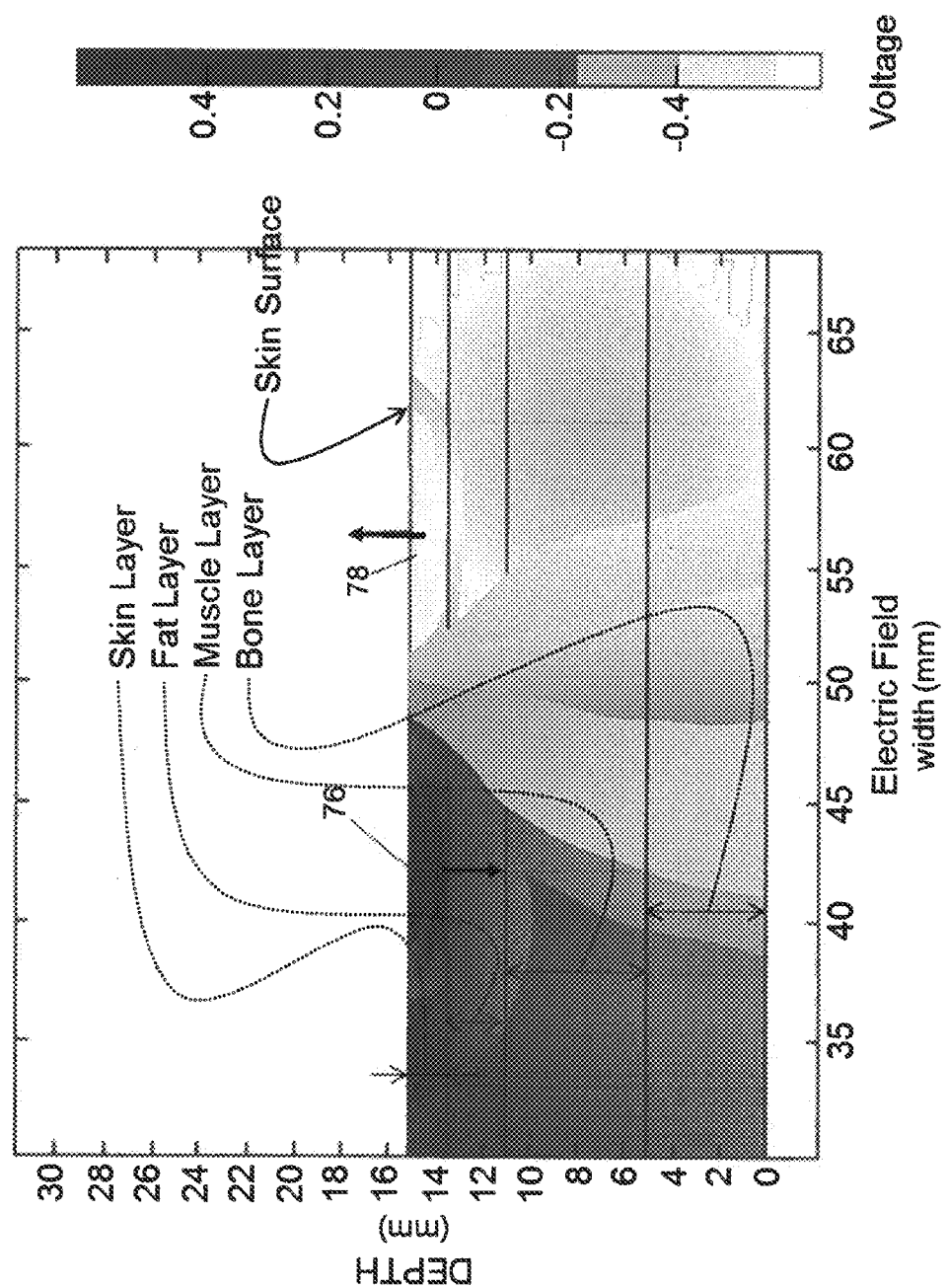
FIG. 11A shows an embodiment illustrating the penetration depth that is achievable with the nerve stimulation device of the present invention.
Figure 11B:
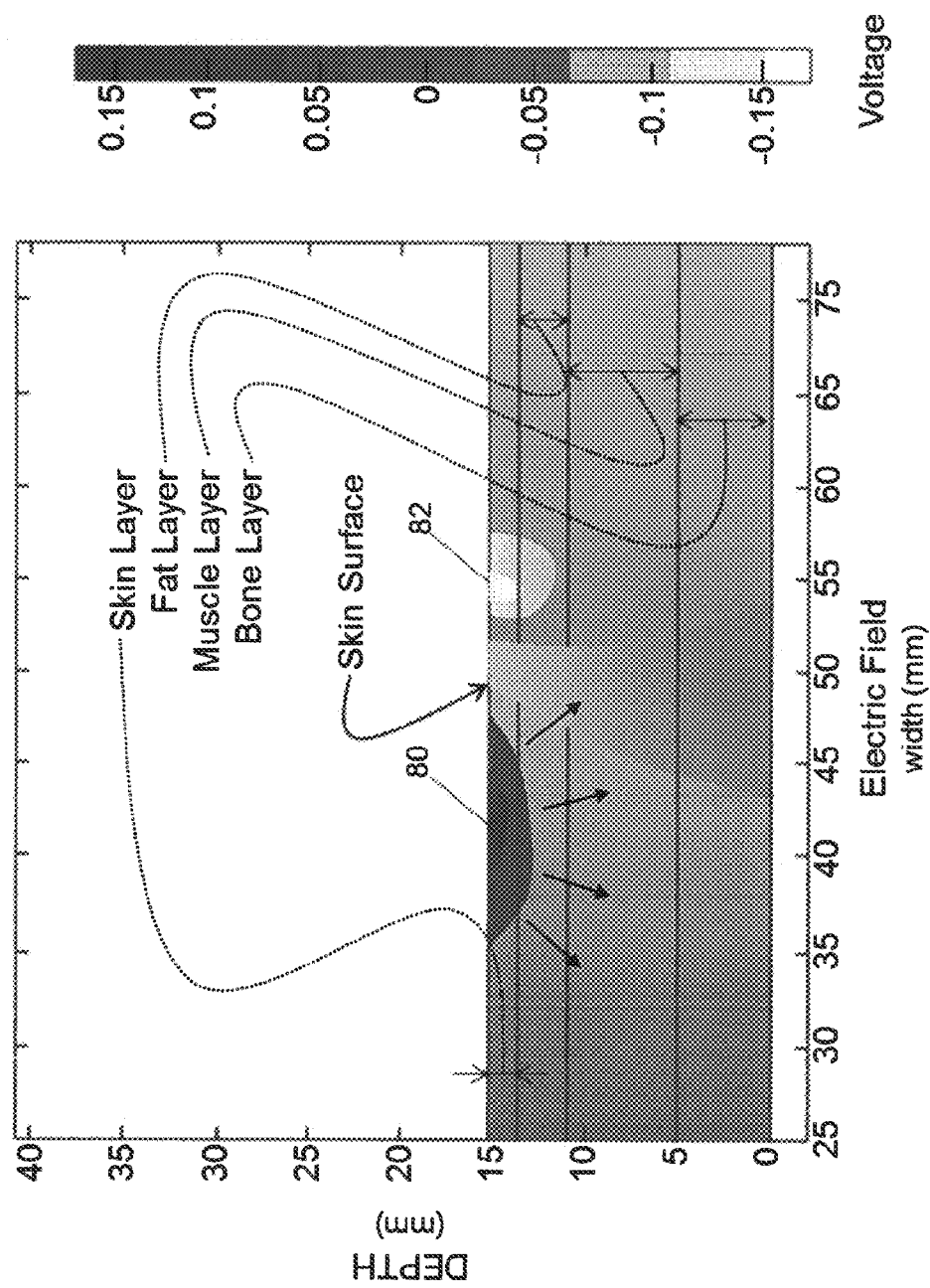
FIG. 11B shows an embodiment illustrating the penetration depth achieved with a percutaneous nerve stimulation device of the prior art.

FIGS. 11A and 11B illustrate the results of computer modeling that was performed to compare the electrical stimulation, i.e., voltage potential and electric field as a function of depth within the skin between the transcutaneous nerve stimulation device 10 of the present invention (FIG. 11A) and a percutaneous nerve stimulation device (FIG. 11B). The percutaneous device was modeled to have a needle with a diameter of about 0.25 mm positioned about 1.5 mm within the skin. The output of the transcutaneous nerve stimulation device 10 of the present invention was modeled to be about 40 mA constant current and the percutaneous stimulation device was model to have a constant current output of about 10 mA.

An equivalent electrical circuit was created to simulate an anatomical construction having a total tissue thickness of about 15 mm. The modeled anatomical construct comprises a layer of skin, having a thickness of about 1.5 mm, a layer of fat having a thickness of about 2.5 mm, a layer of muscle having a thickness of about 6 mm and bone having a thickness of about 5 mm as a function of depth extending from the exterior surface of the skin. The computer model used was based on the work done by Andreas Kuhn disclosed in his 2008 ETH Zurich PhD dissertation entitled "*Modeling Transcutaneous Electrical Stimulation*", the contents of which are incorporated herein by reference.

It is important to note that percutaneous electrical stimulation devices, such as the Urgent PC® device, manufactured by Uroplasty® of Minnetonka Minn. and the Transtim® device, manufactured by EMKinetics® of Mountain View Calif., are designed to invasively penetrate the skin during attachment to the intended area being stimulated. In contrast, the transcutaneous nerve stimulation device 10 of the present invention does not invasively penetrate the skin but rather is contactable to the exterior surface of the skin. Furthermore, percutaneous devices, also in contrast to the present invention, require a clinician to secure the device, hence the patient must make an office or clinic visit for the device to be affixed to the body. As the ankle 12 offers varied articulation of the foot, there is increased possibility for skin damage or tear under pronounced movement, such as running, jumping, cycling, dancing, and the like, which subsequently could lead to infections, cellulitis and other such complications.

Specifically, FIGS. 11A and 11B show the electric fields and associated voltage potential intensities of the transcutaneous and percutaneous electrical stimulation pulses respectively as a function of depth in millimeters within the skin of the ankle 12. As shown, the arrows indicate the direction of the electric field as it travels within the skin. In a preferred embodiment, illustrated in FIG. 11A, the electric field travels from a transcutaneous stimulation "in" position 76, from the first electrode 20A positioned on the external surface of the skin, to a transcutaneous stimulation "out" position 78, the second electrode 20B positioned away from the first electrode 20A on the external surface of the skin. With respect to FIG. 11B, the electric field travels from a percutaneous stimulation "in" position 80, from a first needle positioned within the skin to a percutaneous stimulation "out" position 82, a second needle positioned within the skin. The intensity of the respective voltage potentials of the electrical fields shown in FIGS. 11A and 11B are indicated by the gradient shading shown on the right side of the respective graphs. As shown, the darker the gradient shading, the higher the voltage potential at that location within the field.

As illustrated in FIG. 11A, the transcutaneous input position 76 of the transcutaneous nerve stimulation device 10 of the present invention was modeled to comprise a wider input stimulation region with a higher maximum voltage potential as compared to the percutaneous input stimulation region adjacent to the percutaneous input position 80. As shown in FIG. 11A, the voltage potential was modeled to achieve a maximum voltage of about 0.45 V versus the percutaneous model of FIG. 11B, which indicated a maximum voltage of about 0.15 V. In addition, as illustrated, the transcutaneous input region was modeled have a width of about 15 mm as comparison to about 12 mm for the modeled percutaneous stimulation device. The wider input region of the transcutaneous stimulation device 10 of the present invention is mainly attributed to greater surface area of the substantially "D" electrodes 20A, 20B in comparison to the needle electrodes of the percutaneous device.

Furthermore, as shown in FIG. 11A, the intensity of the voltage potential of the transcutaneous nerve stimulation device 10 of the present invention exhibited less voltage potential decay or rate of voltage stimulation decline as compared to the modeled percutaneous stimulation of FIG. 11B. As shown in FIG. 11A, the voltage potential at about the 15 mm mark of the y axis of the graph was modeled to be about 0.4 V and the voltage potential at the 11 mm mark was modeled to be about 0.3 V, thus the rate of stimulation decay was estimated to be about 0.025 V/mm. In comparison, the modeled percutaneous device had a voltage potential of about 0.15 V at the 15 mm mark of the y axis and a voltage potential of about 0.1 V at about the 14 mm mark, thus the rate of stimulation decay for the percutaneous device was estimated to be about 0.05 V/mm or about double the rate of stimulation decay of the modeled percutaneous device. In addition, the computer modeling revealed that the rate of decay of the voltage potential is largely a function of the position of the needle within the depth of the anatomical construct due to the difference in electrical resistivity of the various layers. Specifically, the computer modeling revealed that positioning the needle of the percutaneous device at a depth of about 6 mm within the body, resulted in an even greater rate of voltage potential decay. Thus, the need to precisely position the needle of the percutaneous device in providing effective electrical stimulation is particularly critical.

Based on the computer modeling analysis illustrated in FIG. 11A, the transcutaneous nerve stimulation device 10 of the present invention is well suited in establishing an electric field and current density to stimulate a nerve, preferably the tibial nerve 26 positioned within the body. As previously mentioned, the transcutaneous nerve stimulator device 10 of the present invention is positioned on the external surface of the skin in contrast to a percutaneous stimulation device having a relatively small needle that is positioned within the skin. The wider electric field and higher voltage potential in combination with the increased surface area of the "D" electrodes, enable the nerve stimulation device 10 of the present invention covers a greater area and can be positioned by the user of the device. In contrast, because the percutaneous stimulation devices comprise relatively small needles, the device must be precisely positioned by a clinician to achieve effective nerve stimulation. In addition, the increased rate of decay of the voltage potential of the percutaneous devices, particularly at differing depths within the skin, increases the need to precisely position the needle within the body to achieve optimal stimulation. If the needle of the percutaneous device is not properly positioned, effective nerve stimulation may not be achieved. Furthermore, if the needle of the percutaneous device were to become dislodged, moved from its intended position, or unintentionally driven further into the skin, effective nerve stimulation might be lost. Consequently, the loss of effective nerve stimulation requires a trip to the clinic or hospital for clinician repositioning and re-engagement of the needle. The present invention with the increased surface area of the electrodes resolves this issue by delivering consistent therapy via the wider electric field, higher voltage potential and less voltage potential decay through the depth of the tissue to the tibial nerve 26.

In summary, the electrical nerve stimulation device 10 of the present invention provides a wider and deeper field of stimulation with less decay as compared to the percutaneous method of the prior art. This improvement in electrical stimulation consistency and penetration, in addition to a wider cross-sectional penetration width, that is achieved by the device 10 of the present invention, increases exposure of the targeted nerve to the stimulation pulse thereby providing improved efficacious therapy. Further contributing to the effectiveness of the therapy delivery to the tibial nerve 26 positioned within the ankle 12, is the improved conformal fit of the housing 14, 52 of the device 10 of the present invention, further improves penetration depth of the electrical stimulation to the tibial nerve 26. Because of the curved, convex shape of the outer surface of the housing 14, 52, the electrodes 20A, 20B of the nerve stimulation device 10 of the present invention offers more intimate contactability to the exterior skin surface 22 of the ankle 12 augmenting nerve stimulation treatment for example, enhanced and even more efficient overactive bladder treatment.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

What is claimed is:

1. A nerve stimulation device for applying electrical stimulation to a nerve, the nerve stimulation device comprising:
   a) a housing having a top surface and an opposing bottom surface that extends from an annular sidewall, wherein the housing bottom surface is curved having a convex shape that outwardly extends away from the opposing top surface, and wherein the curved bottom surface is adapted to be contactable to an exterior surface of a human body;
   b) at least two electrodes received through respective apertures that extend through the housing bottom surface; and
   c) a pulse generating circuit enclosed within the housing operably connected to the electrodes, wherein the pulse generator is capable of generating an electrical pulse.

2. The nerve stimulation device of claim 1 wherein the electrodes are substantially D-shaped having a straight edge and an arcuate edge, the electrodes being arranged within the aperture of the housing with the straight edges opposing each other.

3. The nerve stimulation device of claim 1 wherein at least one strap is attachable to the housing, the strap adapted to secure the housing to the body, wherein the at least one strap is configured relative to the housing and the electrodes so that the electrodes are directly contactable to the skin of the human body when the nerve stimulation device is positioned on the body.

4. The nerve stimulation device of claim 1 wherein a gasket having a first gasket aperture and a second gasket aperture dimensioned to receive the electrodes is disposed about the electrodes on the bottom outer surface of the housing.

5. The nerve stimulation device of claim 1 wherein the housing is composed of a material selected from the group consisting of silicone rubber, acrylonitrile butadiene styrene, styrene, polycarbonate, neoprene and combinations thereof.

6. The nerve stimulation device of claim 1 wherein the housing has a height to width ratio ranging from about 1 to about 3.

7. The nerve stimulation device of claim 1 wherein the housing annular sidewall comprises an outer annular sidewall surface that resides about perpendicular to the top housing surface, wherein the outer annular sidewall surface has a beveled shape that curves distally from the annular sidewall.

8. The nerve stimulation device of claim 1 wherein the pulse generating circuit is configurable to emit a constant current electrical pulse.

9. The nerve stimulation device of claim 1 wherein the electrical pulse comprises a maximum current output of about 60 milliamps.

10. A nerve stimulation device for applying electrical stimulation to a nerve, the nerve stimulation device comprising:
   a) a housing comprising a first housing portion having a first housing portion outer perimeter that extends from a second housing portion having a second housing portion outer perimeter, wherein the second housing portion outer perimeter is greater than the first housing portion outer perimeter;
   b) at least two electrodes positioned on an exterior surface of the second housing portion;

c) a pulse generating circuit enclosed within the first housing portion operably connected to the electrodes to provide an electrical pulse.

11. The nerve stimulation device of claim 10 wherein the at least two electrodes comprise a substantially D-shaped electrodes having a straight edge and an arcuate edge, the electrodes being arranged on the housing with the straight edges opposing each other.

12. The nerve stimulation device of claim 10 wherein the housing is composed of a material selected from the group consisting of silicone rubber, acrylonitrile butadiene styrene, styrene, polycarbonate, neoprene and combinations thereof.

13. The nerve stimulation device of claim 10 wherein the housing has a height to width ratio ranging from about 1 to about 3.

14. The nerve stimulation device of claim 10 wherein the electrical pulse comprises a maximum current output of about 60 milliamps.

15. The nerve stimulation device of claim 10 wherein at least one input mechanism resides within a recessed portion that extends at least partially within an exterior surface of the first housing portion.

16. The nerve stimulation device of claim 10 wherein the first housing portion is removably separatable from the second housing portion.

17. A nerve stimulation device for applying electrical stimulation to a nerve, the nerve stimulation device comprising:
   a) a housing comprising:
      i) a first housing portion having a first housing portion top surface opposed from a first housing bottom surface and a first housing portion outer perimeter; and
      ii) a second housing portion having a second housing portion top surface opposed from a second housing bottom surface and a second housing portion inner perimeter that extends to a second housing portion outer perimeter, wherein the first housing portion is removably positioned within the second housing portion inner perimeter, and wherein the first housing portion bottom surface and the second housing portion bottom surface are about coplanar;
   b) at least two electrodes positioned on the first housing portion bottom surface; and
   c) a pulse generating circuit enclosed within the first housing operably connected to the electrodes, wherein the pulse generating circuit is capable of generating a constant current electrical pulse.

18. The nerve stimulation device of claim 17 wherein at least one input mechanism resides within a recessed portion that at least partially extends within a top surface of the housing.

19. The nerve stimulation device of claim 17 wherein the second housing portion comprises a tab portion that distally extends from the second housing portion outer perimeter.

20. The nerve stimulation device of claim 17 wherein the housing has a height to width ratio ranging from about 1 to about 3.

* * * * *